(12) United States Patent
Morita et al.

(10) Patent No.: US 10,420,360 B2
(45) Date of Patent: *Sep. 24, 2019

(54) STEVIOL GLYCOSIDE

(71) Applicant: MORITA KAGAKU KOGYO CO., LTD., Osaka (JP)

(72) Inventors: Toyoshige Morita, Osaka (JP); Isao Fujita, Osaka (JP); Fumito Matsuura, Hiroshima (JP); Masaya Ota, Hiroshima (JP)

(73) Assignee: MORITA KAGAKU KOGYO CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/826,850

(22) Filed: Nov. 30, 2017

(65) Prior Publication Data

US 2018/0077959 A1    Mar. 22, 2018

Related U.S. Application Data

(63) Continuation of application No. 14/937,329, filed on Nov. 10, 2015, now Pat. No. 9,848,632, which is a (Continued)

(30) Foreign Application Priority Data

Oct. 3, 2008    (JP) .................................. 2008-258617

(51) Int. Cl.
*A23L 27/30* (2016.01)
*C07H 15/256* (2006.01)

(52) U.S. Cl.
CPC .............. *A23L 27/36* (2016.08); *A23L 27/33* (2016.08); *C07H 15/256* (2013.01); *A23V 2002/00* (2013.01); *Y10T 436/143333* (2015.01)

(58) Field of Classification Search
CPC ...... A23L 1/236; A23L 1/2363; A23L 1/2366; A23L 27/36
(Continued)

(56) References Cited

U.S. PATENT DOCUMENTS 4,082,858 A    4/1978  Morita et al.
4,361,697 A   11/1982  Dobberstein et al.
(Continued)

FOREIGN PATENT DOCUMENTS

CN    200610022507.2    6/2008
EP         1856957 A2   11/2007
(Continued)

OTHER PUBLICATIONS

Korean patent application No. 10-2017-7003869, KIPO's Notice of Last Preliminary Rejection (English Translation), dated Apr. 26, 2018.
(Continued)

*Primary Examiner* — Jeffrey P Mornhinweg
(74) *Attorney, Agent, or Firm* — Marshall, Gerstein & Borun LLP

(57) ABSTRACT

Nobel *Stevia* Sweetening components are provided. Through the analysis of the components of the nobel Steviol Glycoside included in the *Stevia* extract and/or crystals, not only the quality control of sweeteners, but judgment on the correctness of indication of origin or infringement of right are facilitated since the raw material of the sweetener can be identified.

21 Claims, 10 Drawing Sheets

Related U.S. Application Data continuation of application No. 14/197,636, filed on Mar. 5, 2014, now Pat. No. 9,215,889, which is a continuation of application No. 13/122,232, filed as application No. PCT/JP2009/067585 on Oct. 2, 2009, now Pat. No. 8,703,225.

(58) Field of Classification Search
USPC .......................................................... 426/548
See application file for complete search history.

(56) References Cited

U.S. PATENT DOCUMENTS

| | | | |
|---|---|---|---|
| 4,892,938 | A | 1/1990 | Giovanetto |
| 6,255,557 | B1 † | 7/2001 | Brandle |
| 8,703,225 | B2 | 4/2014 | Morita et al. |
| 2007/0082103 | A1 | 4/2007 | Magomet et al. |
| 2007/0116823 | A1 | 5/2007 | Prakash et al. |
| 2008/0300402 | A1 | 12/2008 | Yang et al. |
| 2009/0214753 | A1 | 8/2009 | Morita et al. |
| 2011/0076239 | A1 | 3/2011 | Reichelt et al. |
| 2014/0187761 | A1 | 7/2014 | Morita et al. |

FOREIGN PATENT DOCUMENTS

| | | | |
|---|---|---|---|
| EP | 1856967 | A1 | 11/2007 |
| EP | 22980584 | A1 | 3/2011 |
| JP | 01-319494 | | 12/1989 |
| JP | 06-094473 | | 4/1994 |
| JP | 2003-009878 | A | 1/2003 |
| WO | WO-2006/093229 | A1 | 9/2006 |
| WO | 2008/091547 | A2 † | 7/2008 |
| WO | WO-2009/108680 | A2 | 9/2009 |
| WO | WO-2009/149577 | A1 | 12/2009 |
| WO | WO-2010/038911 | A1 | 4/2010 |

OTHER PUBLICATIONS

Korean patent application No. 10-2017-7003870, KIPO's Notice of Last Preliminary Rejection (English Translation), dated Apr. 26, 2018.
Kamiya et al., Synthesis and tase of some analogs of stevioside. Agric. Biol. Chem. 43(9): 1863-7 (1979).
Kasai et al., Sweet diterpene-glycosides of leaves of Stevia rebaudiana Bertoni synthesis and structure-sweetness relationship of rebaudiosides-A, -D, -E and their related glycosides. Nippon Kagaku Kaishi, 5: 726-35 (1981)—English Abstract Only.
Kobayashi et al., Dulcosides A and B, new diterpene glycosides from Stevia rebaudiana. *Phyrochemistry*, 16: 1405-8 (1977).
Koyama et al., In vitro metabolism of the glycoside sweeteners, stevia mixture and enzymatically modified stevia in human intestinal microflora. *Food and Chemical Toxicology*, 41: 359-74 (2003).
Kusama et al., Transglucosylation into stevioside by the enyzme system from streoptomyces sp. *Agric. Biol. Chem.* 50(10): 2445-51 (1986).
Ohta et al., Characterization of novel steviol glycosides from leaves of Stevia rebaudiana Morita. *J. Appl. Glycosci.* 57: 199-209 (2010).

Prakash et al., Isolation and Characterization of a Novel Rebaudioside M Isomer from a Bioconversion reaction of Rebaudioside A and NMR Comparison Studies of Rebaudioside M Isolated from *Stevia rebaudiana* Bertoni and *Stevia rebaudiana* Morita, *Biomolecules*, 4:374-89 (2014).
Rajasekaran et al., Analysis of Predominant Steviosides in *Stevie rebaudiana* Bertoni by Liquid Chromatography/ Electrospray Ionization-Mass Spectrometry, *Food Biotechnology*, 22:179-88 (2008).
Semma et al., Development of Rapid Analyses of Stevia Sweetners and an Approach to Study the Metabolism of the Component of Stevia by Intestinal Microbes, Jap. J. Food Chem., 8(2):105-11 (2001).
Starratt et al., Rebaudioside F, a dierpene glycoside from *Stevia rebaudiana, Phytochemistry*, 59:367-70 (2002).
Steviol Glycosides, Compendium of Food Additives Specificaitons, FACO JECFA Monographs, 4: 61-4 (2007).
Wölwer-Rieck, The leaves of Stevia rebaudiana (*Bertoni*), their constituents and the analysis thereof: A review. *J. Agric. Food Chem.* 60: 886-95 (2012).
Extended European Search Report, EP 16161536.4, dated Sep. 21, 2016.
Extended European Search Report dated Feb. 28, 2013 issued in European Patent Application No. 09817935.1.
International Search Report and Written Opinion dated Jan. 19, 2010 issued in PCT Patent Application No. PCT/JP2009/067585.
International Preliminary Report on Patentability dated Apr. 5, 2011 issued in PCT Patent Application No. PCT/JP2009/067585.
Office Action dated Oct. 5, 2012 issued in U.S. Appl. No. 13/122,232.
Office Action dated Jan. 30, 2013 issued in CN Patent Application No. 200980139481.1.
Office Action dated May 22, 2013 issued in U.S. Appl. No. 13/122,232.
Office Action dated Nov. 7, 2013 issued in U.S. Appl. No. 13/122,232.
Office Action dated Jan. 5, 2015 issued in U.S. Appl. No. 14/197,636.
Preliminary Rejection Issued in KR 10-2017-7003869, dated Jun. 9, 2017.
Preliminary Rejection Issued in KR 10-2017-7003870, dated Jun. 9, 2017.
European Patent No. 2350110, Communication of Further Notices of Opposition Pursuant to Rule 79(2) EPC, dated Apr. 25, 2017.
European Patent No. 2350110, European Patent Office's Opposition Division Decision, dated Jul. 30, 2018.
European Patent No. 2350110, New Auxiliary Requests 5 and 6, dated May 29, 2018.
European Patent No. 2350110, Notice of Opposition to a European Patent, dated Mar. 15, 2017.
European Patent No. 2350110, Opponent's Grounds for Appeal, dated Dec. 7, 2018.
European Patent No. 2350110, Opponent's Response, dated Jun. 22, 2018.
European Patent No. 2350110, Patentee's Response to Appeal, dated Apr. 23, 2019.
European Patent No. 2350110, Patentee's Response to the Communication of Notices of Opposition, dated Oct. 5, 2017.
European Patent No. 2350110, Reponse to the Summons to Attend Oral Proceedings, dated Apr. 26, 2018.
Official Action dated Feb. 11, 2019 in Chinese Patent Application No. 201611198318.0 (with English Translation).

† cited by third party

[Fig. 1]
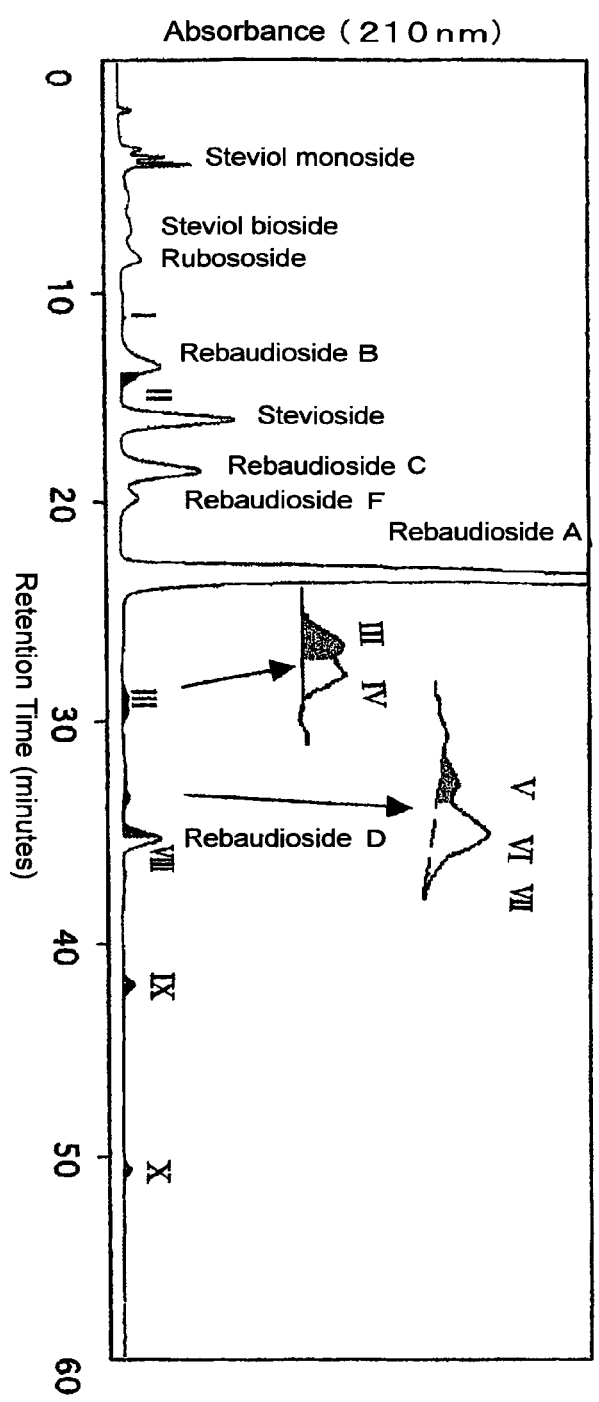

[Fig. 2]
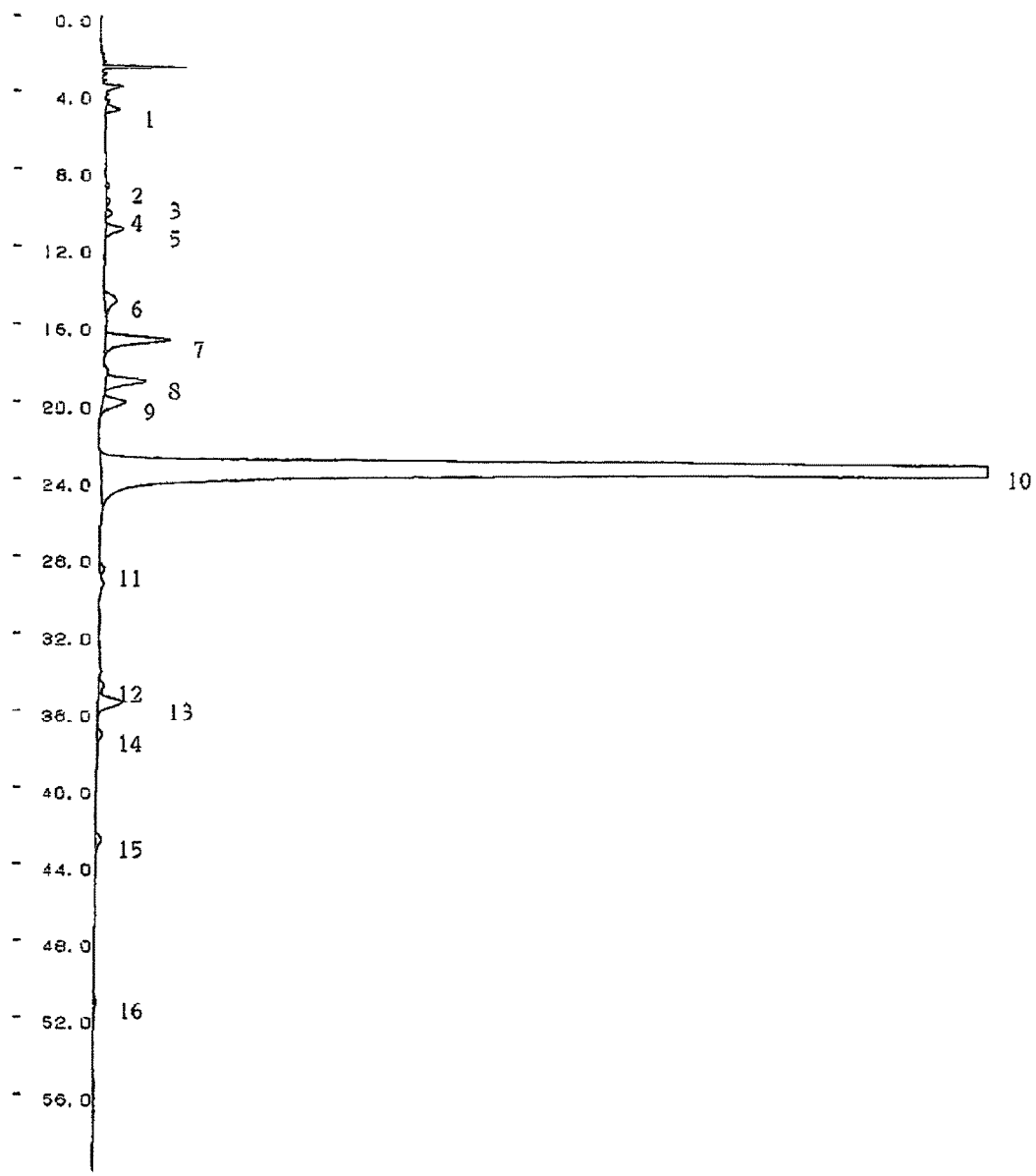

[Fig. 3]
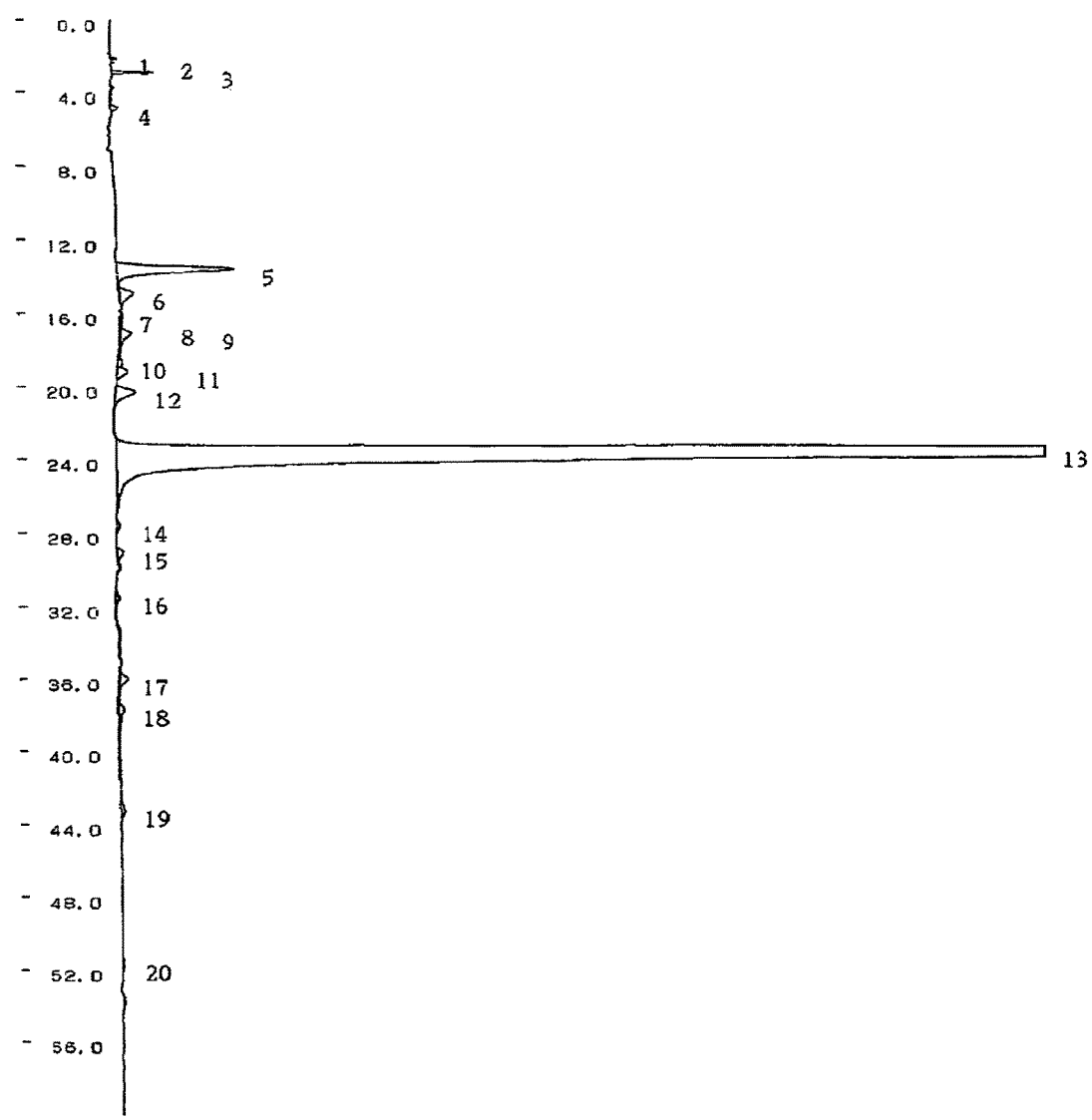

[Fig. 4]
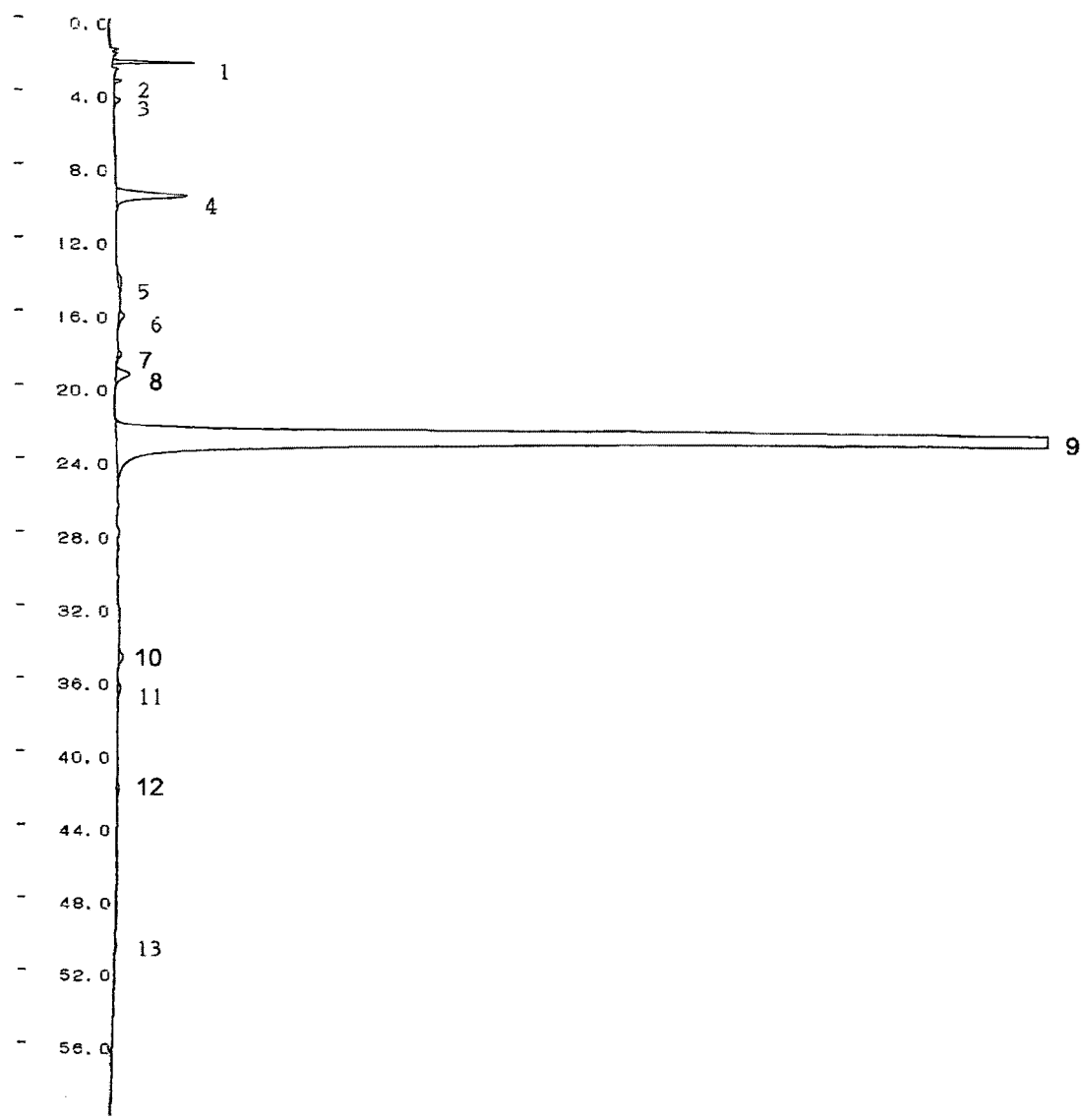

[Fig. 5]
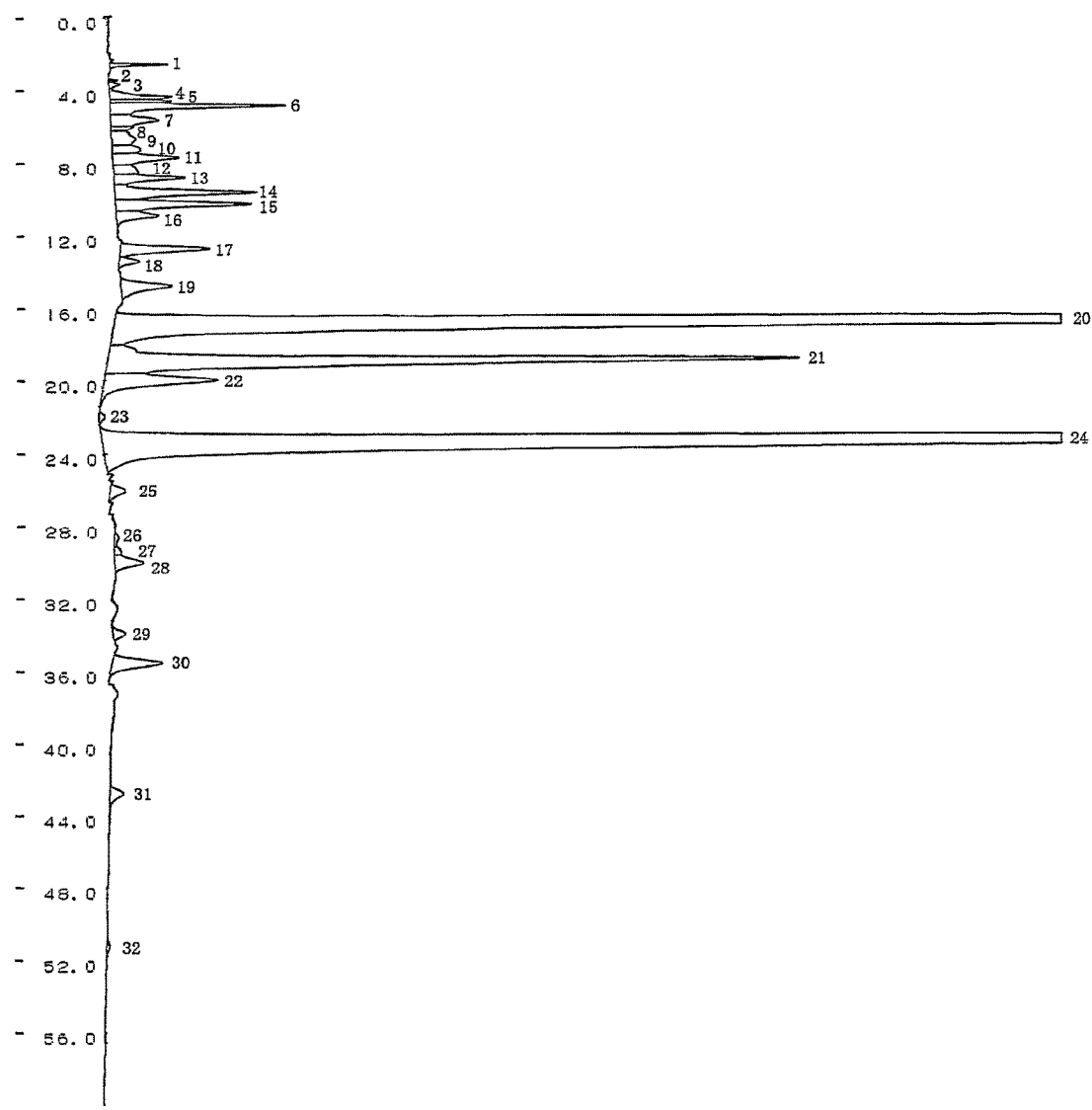

[Fig. 6]
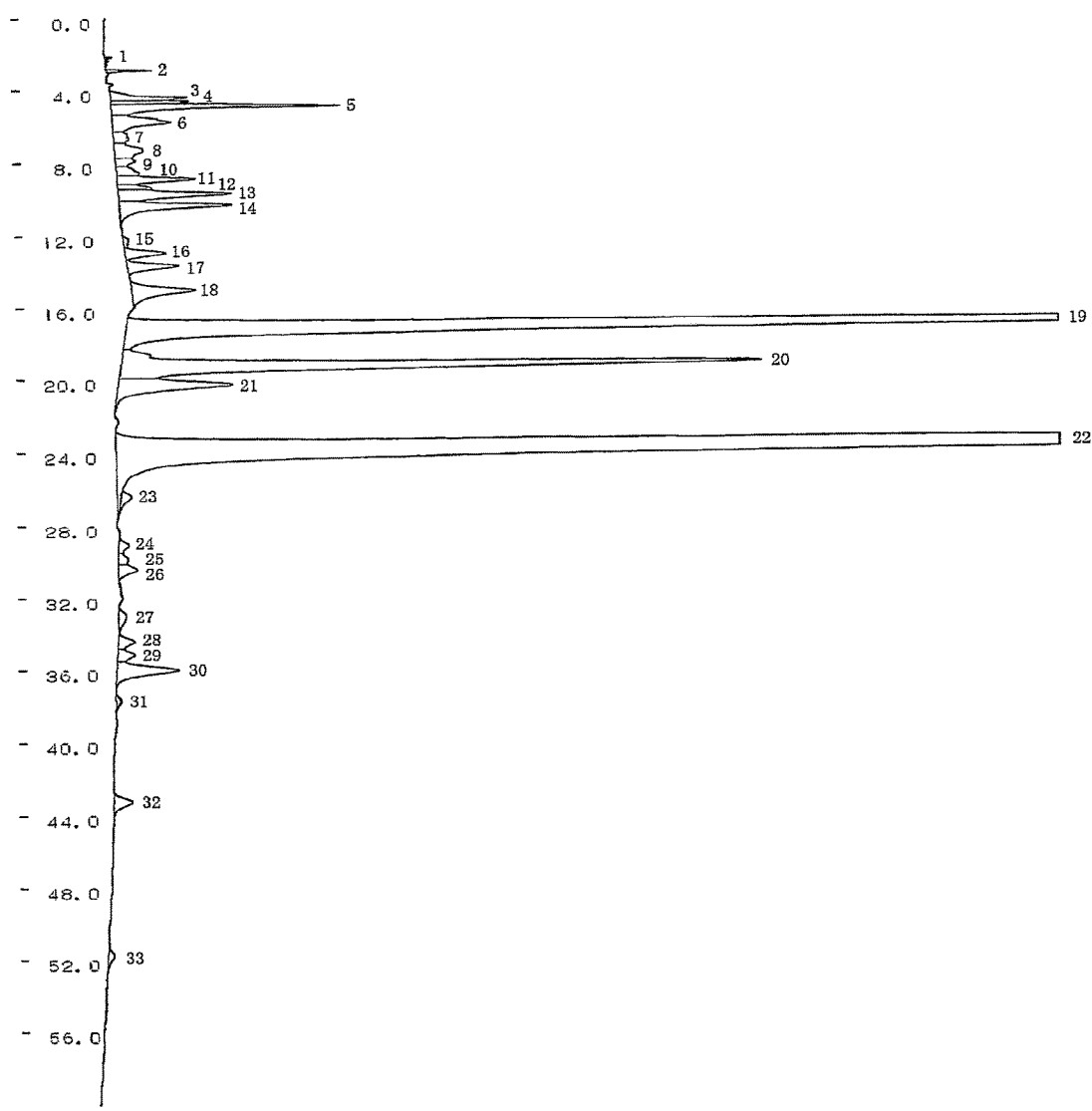

[Fig. 7]
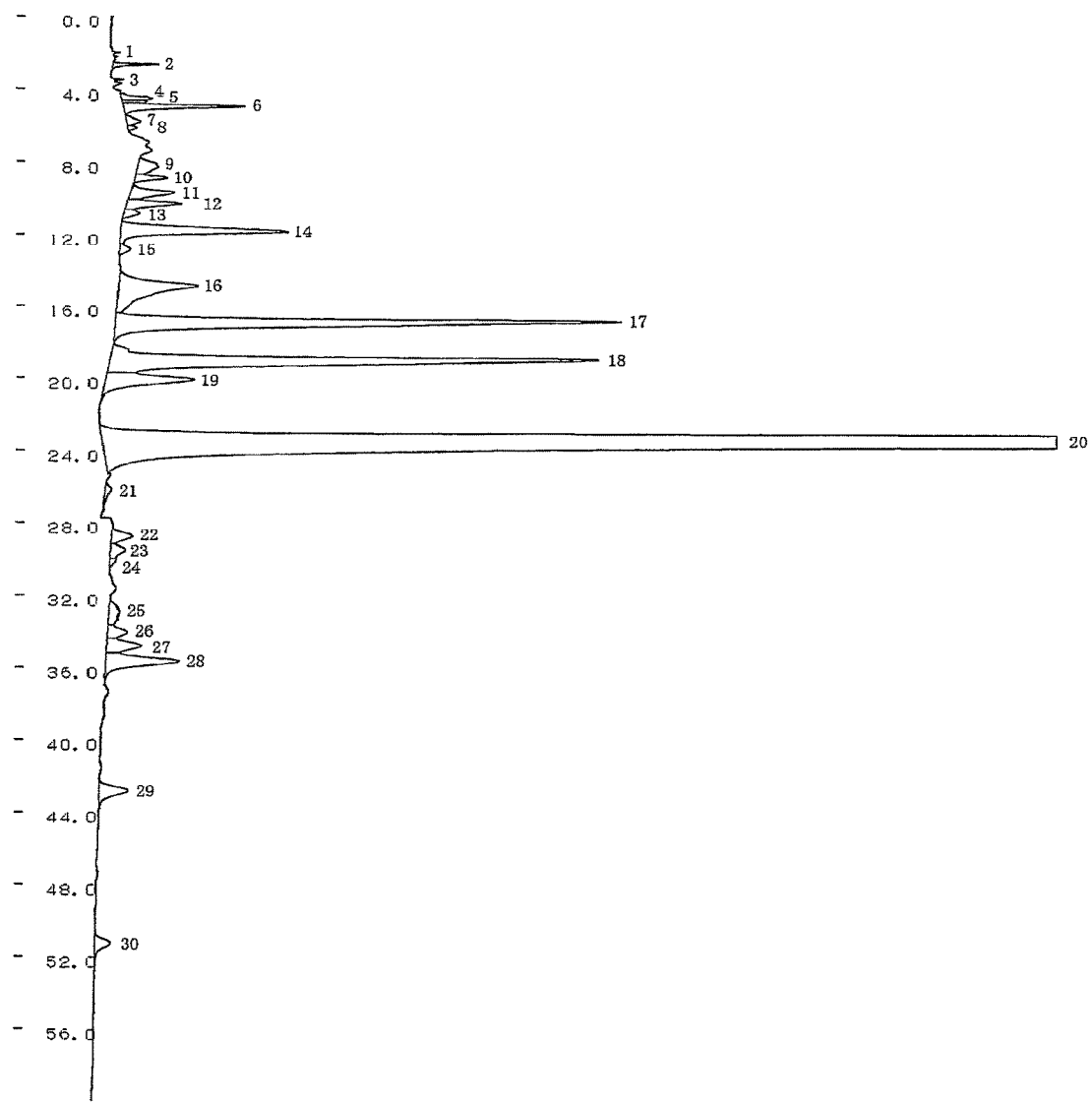

[Fig. 8]
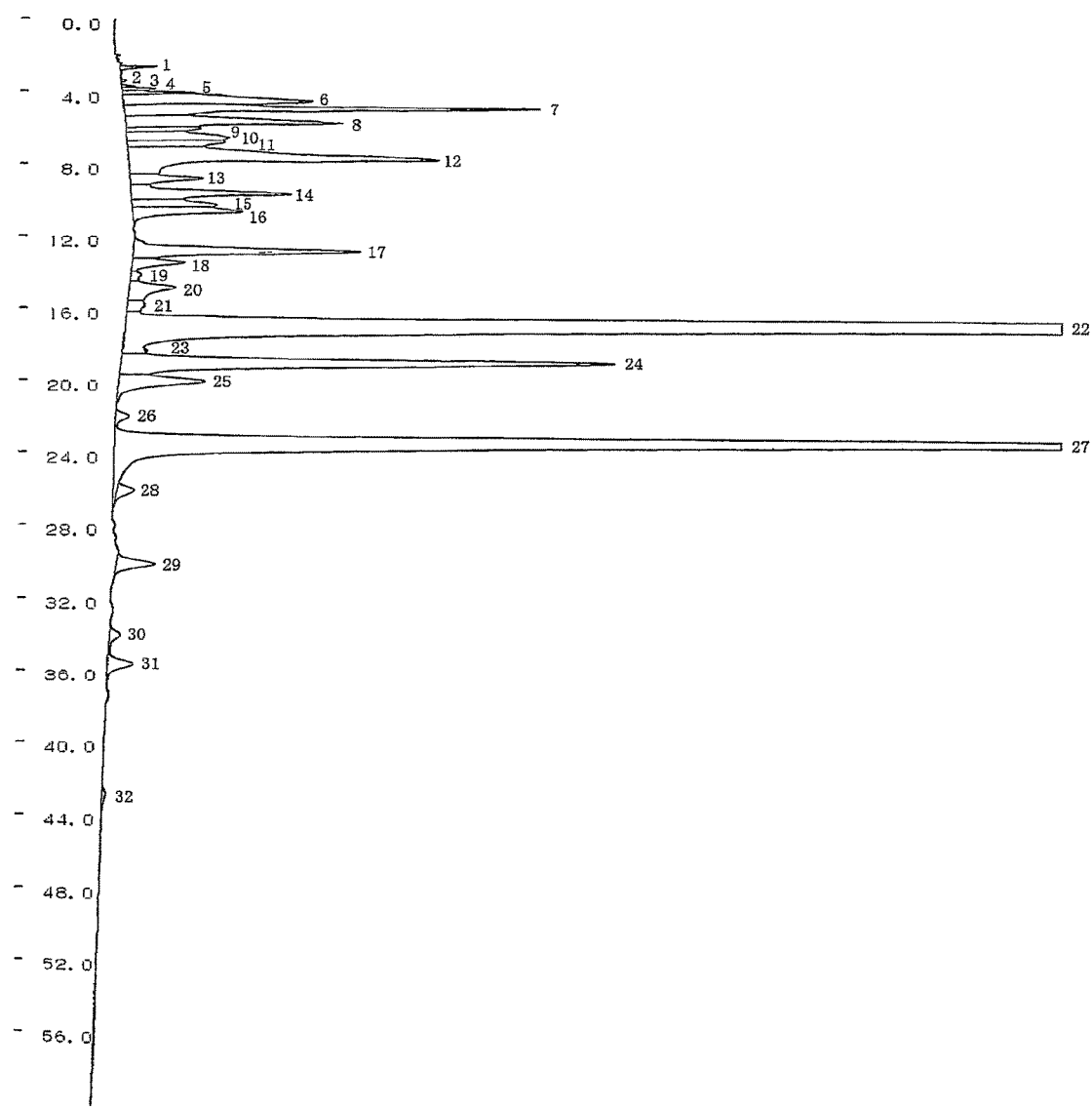

[Fig. 9]
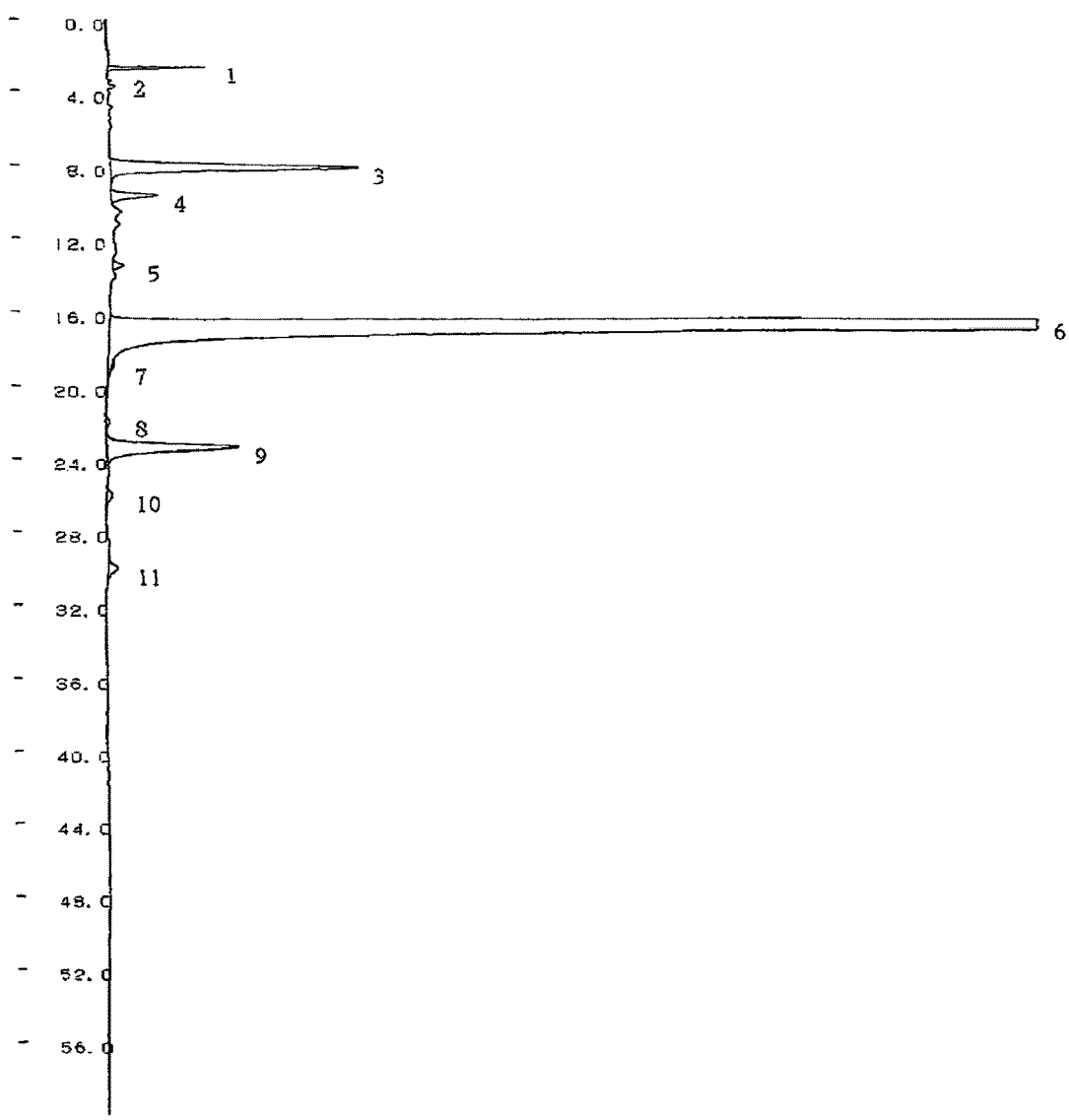

[Fig. 10]
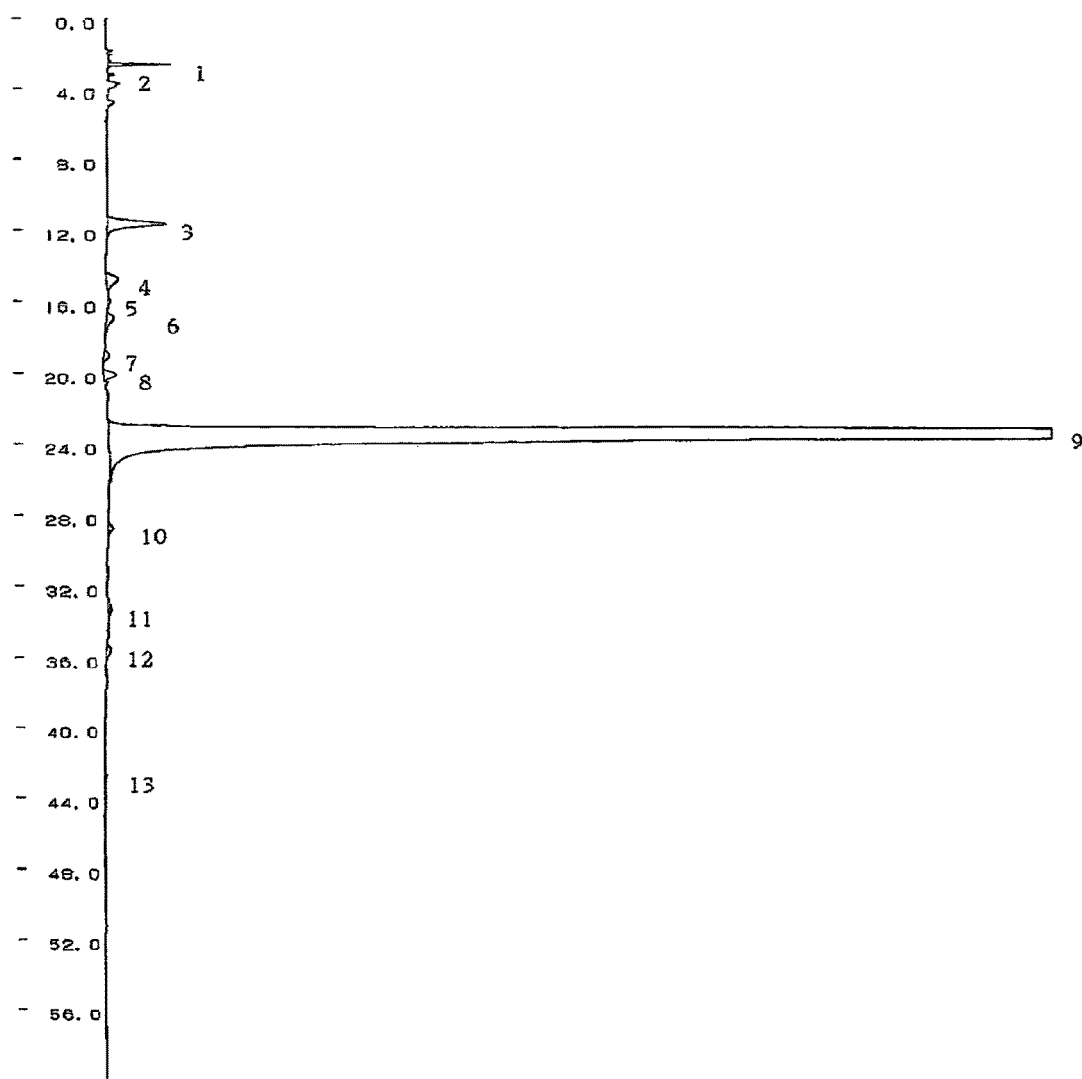

STEVIOL GLYCOSIDE

TECHNICAL FIELD

The present invention relates to a novel Steviol Glycoside, a sweetener containing Rebaudioside A and the novel Steviol Glycoside, which is included in the variety *Stevia rebaudiana* Bertoni containing a high content of Rebaudioside A, a method of manufacturing food, pharmaceuticals, non-pharmaceuticals and cosmetics, confirmation of *Stevia* varieties and analytical method of the novel Steviol Glycoside.

BACKGROUND ART

*Stevia* is a perennial plant of the Asteraceae family grown in Paraguay, South America. Its scientific name is *Stevia rebaudiana* Bertoni. *Stevia* contains components, whose sweetness is 300 times or more than that of sucrose and is planted to be used as a natural sweetener after extracting the sweet components.

Stevioside ($C_{38}H_{60}O_{18}$), Rebaudioside A ($C_{44}H_{70}O_{23}$). Rebaudioside C, D and E, Dulcoside A etc. have been known as sweet components of *Stevia*. In the generally planted *Stevia* variety, Stevioside (hereinafter ST) is the major component among the aforementioned sweet components, with a contained amount of Rebaudioside A (hereinafter RA) of around 40 weight % content and that of Rebaudioside C being slightly less. But depending on the variety there are various types such as those with Rebaudioside C being the major component.

Because ST has a degree of sweetness of 300 times that of sucrose, it has been widely used in the food industry as a natural sweetener. Its sweetness is relatively similar to that of sugar, but it is known that compared to RA an unpleasant taste of bitterness remains in the mouth. Compared to this, RA has good quality of sweetness, with a degree of sweetness from 1.3 to 1.5 time that of ST, so in general a sweetener of *Stevia* with a high RA content ratio is desirable rather than ST. The inventors of the present invention carried out plant breeding through the repetition of selective cross fertilizations of conventional varieties, thereby obtaining only *Stevia* varieties with very few amounts of ST compared to RA, developing sweeteners from these varieties (see Patent Literature 1 for example).

However, among the tastes such as bitterness, astringency and smoothness to the tongue, the smooth taste is quite delicate. This delicate smoothness does not rely upon the ratio between ST and RA alone. When glucose is added to the chemical structure of the various sweet components contained in *Stevia*, the smooth taste is improved and a method has been developed to improve the smooth and strong tastes by structurally adding glucose to the sweet components of *Stevia* (Patent Literature 2 and 3).

Thus, even if the content amount is small, it is very important to analyze the unknown components contained in *Stevia*, in particular to grasp the components in which glucose is structurally added rather than ST, and it is extremely important to execute a careful examination of the glucose structurally added to them from a perspective of taste-quality control.

Simultaneously, as the taste quality is influenced by the sweet components included in the raw material plants themselves, it is important to grasp thoroughly the sweet components in order to develop excellent *Stevia* varieties and use them. From now on, raw material plant improvement of breed will probably become very popular, but it will be possible to grasp in details the results of the breed improvement by specifying diligently the sweet components contained in the plants developed.

On the other hand, the inventors of the present invention developed a method for establishing a variety for plant varieties newly developed by using genes (Patent Literature 4 and 5), but actually there were no means of specifying the raw material plants regarding the sweetener extracted and processed from these raw material plants and the products which make use of them.

[Patent Literature 1] Laid Open Patent Publication JP2002-262822 Gazette

[Patent Literature 2] Patent Publication JP1957-18779 Gazette

[Patent Literature 3] Laid Open Patent Publication JP1997-107913 Gazette

[Patent Literature 4] Laid Open Patent Publication JP2003-009878, Gazette

[Patent Literature 5] International Patent Publication of Patent Cooperation Treaty-PCT WO06/093229 Gazette

DISCLOSURE OF INVENTION

Problems to be Solved

Five components of the *Stevia* sweetener (ST, RA, Rebaudioside A, Dulcoside A and Steviol Bioside) have been analyzed and standardized, but there was no knowledge on the other unknown components. In addition, there was no way to confirm their presence even for the sweet components already known, since there was no established analytical method. However, recently the JECFA standard has been set for 7 components of Steviol Glycoside, the sweeteners contained in *Stevia* have been confirmed and the unknown components clarified, along with the awareness on the importance to know the influence of the delicate taste from these components.

The purpose of the present invention is to define the structure of the small quantity sweeteners contained in the *Stevia* variety and to confirm their influence on the taste for *Stevia* sweetener.

Also the other purpose is to provide the measures for specifying the *Stevia* plant, which became a raw material, regarding *Stevia* sweetener and the products which use it.

The inventors of the present invention have searched new Steviol Glycosides contained in the *Stevia* variety, main component of which is RA, and discovered 10 components of the novel Steviol Glycosides which may have a subtle influence on taste quality. After then they completed the present invention by discovering that there was a difference in content volume of these components among varieties, and certain components were present only in the specified *Stevia* varieties which had RA as their main component followed by confirmation that it was possible to use this as a marker of sweetener originated in such plants.

Effects of the Invention

Steviol Glycosides of the present invention have structures in which more glucoses are added than ST or RA and therefore provide a *Stevia* sweetener having an excellent strong taste.

Besides, it is possible to suppose the origin of the raw material by confirming Steviol Glycoside X in the extract or the crystals, and analysis of the final product enables to judge if the raw material plant is opposed to rights such as patent and others.

(The Best Mode for Embodying the Invention)

The *Stevia* variety with RA as main component mentioned in the present invention is a variety which contains more RA content than ST, and described in the applications for patent JP2001-200944 and JP2007-506004; the extract obtained from dry leaves has more RA content than ST and also contains Rebaudioside D (R-D), Steviol Glycoside III, V, VI, VII and X, making it possible to obtain an excellent sweetener of strong taste by containing the component in which more glucoses are structurally added than ST and/or RA.

In addition, it is possible to efficiently obtain highly pure RA sweetener containing a trace amount of ST and Steviol Glycoside X by recrystalization.

The first embodiment of the present invention is Steviol Glycoside of the formula I to X:

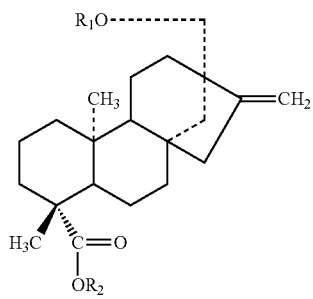

I-X wherein $R_1$ and $R_2$ are a hydrogen atom or a sugar chain defined in the next table;

| No. (Steviol Glyciside) | $R_1$ | $R_2$ |
|---|---|---|
| I (Dulcoside B) | β-glc-α-rha(2→1)\\β-glc(3→1) | H |
| II (Rebaudioside G) | β-glc-β-glc(3→1) | β-glc |
| III (Rebaudioside I) | β-glc-β-glc(2→1)\\β-glc(3→1) | β-glc-β-glc-(3→1) |
| IV (Rebaudioside H) | β-glc-α-rha(2→1)-β-glc(3−1)\\β-glc(3−1) | β-glc |
| V (Rebaudioside L) | β-glc-β-glc(2−1)\\β-glc(3−1) } β-glc(6−1) | β-glc |
| VI (Rebaudioside K) | β-glc-α-rha(2→1)\\β-glc(3→1) | β-glc-β-glc(2→1) |
| VII (Rebaudioside J) | β-glc-β-glc(2→1)\\β-glc(3→1) | β-glc-α-rha(2→1) |
| VIII (Rebaudioside M) | β-glc-β-glc(2→1)\\β-glc(3→1) | β-glc-β-glc(2→1)\\β-glc(3→1) |
| IX (Rebaudioside N) | β-glc-β-glc(2→1)\\β-glc(3→1) | β-glc-α-rha(2→1)\\β-glc(3→1) |
| X (Rebaudioside O) | β-glc-β-glc(2→1)\\β-glc(3→1) | β-glc-α-rha(2→1)-β-glc(3→1)\\β-glc(3→1) |

The symbols in the formula are the sugar below:
glc: D-glucopyranosyl
rha: L-rhamnopyranosyl
xyl: xylopyranosyl The second embodiment of the present invention is an extract containing Steviol Glycoside X (Rebaudioside O), obtained by extracting a plant body of *Stevia rebaudiana* Bertoni, a plant of the Asteraceae family, or its dry leaves, a main component of which is Rebaudioside A, by water or a solvent containing water.

The third embodiment of the present invention is a method of obtaining highly pure Rebaudioside A containing Steviol Glycoside X (Rebaudioside O) through the recrystalization of the extract of the aforementioned embodiment.

The fourth embodiment of the present invention is a manufacturing method for foodstuff, in which the extract of the second embodiment above is added to food in an amount of equal to or less than 1% of the food.

The fifth embodiment of the present invention is a manufacturing method for foodstuff, in which the highly pure Rebaudioside A obtained in the third embodiment above is added to food in an amount of equal to or less than 1% of the food.

In the extract obtained from the raw material variety, whose main component is ST, there is no Steviol Glycoside X, but as the extract obtained from raw material varieties, whose main component is RA, has Glycoside X, it is possible to judge the raw material variety by whether the main component is ST or RA. That is, as there is no Glycoside X in the extract containing RA as a main component, which is obtained by eliminating ST by crystallization through the extract obtained from varieties whose main component is ST, or in the high purity products obtained from their recrystalization, it is possible to confirm the raw material varieties. The sixth embodiment of the present invention is the method for confirming *Stevia* varieties by Steviol Glycoside X.

The seventh embodiment of the present invention is an analytical method of the Steviol Glycosides I-X through high performance liquid chromatography (hereinafter HPLC).

In order to accomplish these objectives, the inventors of the present invention extensively studied the sweet components included in the varieties whose main component is RA and the varieties of applications JP2001-200944 and JP2007-506004, found new sweet components and determined their chemical structure. In addition, they confirmed the usefulness of these components as sweeteners and completed the analytical method and confirmation method of varieties through these varieties.

The confirmation of the new components was executed through extraction by water or solvent containing water of the varieties whose main components was RA as in the Example 1 (hereinafter called Variety A) and the dry leaves of applications JP2001-200944 (hereinafter called Variety B) and 2007-506004 (hereinafter called Variety C).

After that, the extract solution is directly concentrated, or if necessary, ionic impurities are removed with an ionic exchange resin or a cationic exchange resin, or activated carbon, the sweetening components are allowed to be absorbed into an absorption resin, followed by the elution with a hydrophilic solvent, and if necessary the elute is concentrated and dried and the eluant retreated with an ionic exchange resin or a cationic exchange resin, or activated carbon, and the extract thus obtained or the extract obtained through an appropriate purification means of conventional art such as discoloring can be confirmed.

The novel Steviol Glycosides of the extract RA-C obtained from the Example 1(1) described hereinafter were separated and analyzed by a device of High performance liquid chromatography mass spectrometry (HPLC-MS) according to Example 5 and each Glycoside structure I-X:

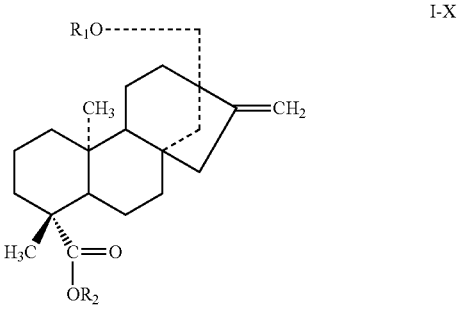

wherein $R^1$ and $R^2$ are respectively a hydrogen atom and the aforementioned sugar chain, was determined.

Steviol Glycoside I (Dulcoside B) is a glycoside with a structure of 788 molecular weight, as confirmed by about minutes of chromatograph Retention Time (hereinafter R.T.) of the HPLC in FIG. 1.

Steviol Glycoside II (Rebaudioside G) is a glycoside with a structure of 804 molecular weight, as confirmed by about 15 minutes of R.T. of HPLC in FIG. 1.

Steviol Glycoside III (Rebaudioside I) is a glycoside with a structure of 1112 molecular weight, as confirmed by about 28 minutes of R.T. of HPLC in FIG. 1.

Steviol Glycoside IV (Rebaudioside H) is a glycoside with a structure of 1128 molecular weight, as confirmed by about 29 minutes of R.T. of HPLC in FIG. 1.

Steviol Glycoside V (Rebaudioside L) is a glycoside with a structure of 1112 molecular weight, as confirmed by about 34 minutes of R.T. of HPLC in FIG. 1.

Steviol Glycoside VI (Rebaudioside K) is a glycoside with a structure of 1112 molecular weight, as confirmed by about 34 minutes of R.T. of HPLC in FIG. 1.

Steviol Glycoside VII (Rebaudioside J) is a glycoside with a structure of 1128 molecular weight, as confirmed by about 34 minutes of R.T. of HPLC in FIG. 1.

Steviol Glycoside VIII (Rebaudioside M) is a glycoside with a structure of 1290 molecular weight, as confirmed by duplicating Rebaudioside D by about 34 minutes of R.T. of HPLC in FIG. 1.

Steviol Glycoside IX (Rebaudioside N) is a glycoside with a structure of 1274 molecular weight, as confirmed by about 43 minutes of R.T. of HPLC in FIG. 1.

Steviol Glycoside X (Rebaudioside O) is a glycoside with a structure of 1436 molecular weight, as confirmed by about 51 minutes of R.T. of HPLC in FIG. 1.

However, anyone skilled in the art will understand that the R.T. mentioned above from the analysis using gradient elution is variable.

As mentioned above, it provides with important information for the identification of the raw material variety whether Steviol Glycoside X is present or not in the final product.

Simultaneously, since it is possible to confirm these novel Steviol Glycosides through HPLC, even in case they are used as sweeteners, quality and taste may be totally controlled with ease by HPLC analysis.

The extract or crystals obtained may be used as sweetener in candies, jellies, powder beverages, instant noodles, jams, frozen fruits, chewing gums, Japanese sweets, health foods, chocolate, tabletop sweeteners, fried sweets, delicacies, water boiled foods, fermented lactic-drink, coffee drinks, cocoa drinks, tea drinks, liqueurs, wines, sherbets, cereals, vegetable fiber-containing foods, sauces, soy sauce, soy paste, vinegars, dressings, mayonnaises, catch-up, curry, soups, rice sweets, arare, breads, biscuits, crackers, pancake mix, canning fruits, canning vegetables, meat products, products made with boiled fish paste, salt foods, pickles, combined seasoning, luxury foods, cosmetics, etc, resulting in calorie decrease, sucrose reduction, melting point decrease, improvement of sweetness quality and masking effect, among others, also being possible to be added to other natural and artificial sweeteners and solvents.

EXAMPLES

Example 1 Manufacturing of RA Extract (1) Extract 100 g of dry leaves obtained from varieties A, B or C, whose main component is RA, was extracted several times with 20 times amount of water by weight until the sweetness cannot be tasted. The extract was passed through a column filled up with 300 ml of absorption resin (Diaion HP-20) and the sweet components of the extract were absorbed to the resin, which was sufficiently washed with water, and the components were eluted with 900 ml of methanol. The eluate was passed through a column filled up with 200 ml of ion exchange resin (Diaion WA-30), 10 g of activated carbon was added to the eluate and stirred. The mixture was filtered, the filtrate was concentrated and the residue was dried to give 13.0 g of RA-A extract, whose main component is light yellow Rebaudioside A (ST 35.4%, RA 41.7% and RC 9.8%), 11.5 g of RA-B extract (ST 19.5%, RA 58.1% and RC 8.8%) and 12 g of RA-C extract (ST 5.4%, RA 72.3% and RC 8.1%) respectively.

(2) RA Recrystallization

Each 5 g of the aforementioned RA-B extract and RA-C extract was dissolved in 10 times the weight of 90% methanol under heating, and it was left stand at 4° C. for six days. The resulted crystals were separated, washed with cold methanol and dried under reduced pressure to give 3.9 g of white RA-B crystals (ST 0.2%, RA 95.0% and RC 0.2%) and 4.5 g of RA-C Crystals (ST 0.2%, RA 95.6% and RC 0.1%) respectively.

Example 2 Manufacturing of ST Extract

For comparison purposes, the same procedure was carried out as to a variety, the main component of which is ST, to give 11.3 g of ST extract (ST 51.9%, RA 23.7% and RC 7.4%).

Example 3 RA-A Mother Liquid, ST Mother Liquid

Each 10 g of the aforementioned RA-A extract and ST extract was dissolved in 10 times the weight of 90% methanol under heating, and it was left stand at 4° C. for six days. The resulted crystals were separated, washed with cold 98% methanol and dried under reduced pressure to give 2.1 g of RA-ST crystals, which are white crystals of stevioside, and 3.8 g of ST-ST crystals respectively.

Each of 8.8 g of RA-A mother liquid (ST 15.7%, RA 43.8% and RC 6.9%) and 6.1 g of ST mother liquor (ST 20.0%, RA 37.1% and RC 11.2%), whose main component is RA, is concentrated and dried to give a powder of mother liquid, whose main component was a pale yellow RA respectively.

Example 4 RA-A Crystal, ST-RA Crystal

Each of the mother liquid powder of Example 3 was dissolved in 10 times the weight of 90% methanol under heating and left stand at 4° C. for six days. The resulted crystals were separated, washed with cold 98% methanol and dried under reduced pressure to give 2.2 g of white RA-A crystals (ST 1.6%, RA 90.4% and RC 1.4%) and 1.2 g of ST-RA crystals (ST 1.6%, RA 96.9% and RC 1.4%) respectively.

Example 5 Structural Determination of Steviol Glycosides

As described below, analysis was performed by using HPLC. Separation of the Steviol Glycosides included in each extract was carried out by using Shimazu LC-10 Advp HPLC using a column of TSKgel Amide-80 (4.6×250 mm Tosoh). Acetonitril-water was used as a solvent and a gradient elution in which the ratio of acetonitril:water was changed from 82:18 to 66:34 within 60 minutes was carried out. The flow rate was 0.65 ml/min, the column temperature was 40° C. and the detection was performed at ultraviolet absorption of 210 nm.

In the measurement of molecular weight, Waters' Alliance HPLC System 2695 and Waters' Quattro micro (triple quadrupole mass) equipped with electrospray ionization (ESI)-mass spectrometer were used. As to HPLC, a column was TSKgel Amide-80 (2.0×250 mm, Tosoh), acetonitril-water was used as a solvent and a gradient elution in which the ratio of acetonitril:water was changed from 82:18 to 66:34 within 60 minutes was carried out. The flow rate was 0.2 ml/min, the column temperature was 40° C. Nitrogen gas was used as a desolvation gas and argon gas was used as a collision gas. As a capillary voltage, 15.0 kV were used in the Steviol Glycoside analysis in the negative mode and in the analysis of ABEE-oligosaccharides 13.5 kV were used in the positive mode. A voltage of 10V to 80V was used as the cone voltage and the collision voltage at the time of MS/MS analysis. The source temperature and desolvation temperature were 100° C. and 400° C. respectively and the flow volume of cone gas and desolvation gas were 50 l/hr and 900 l/hr respectively.

The results of HPLC Analysis regarding each extract and crystal were illustrated in FIGS. 1-10.

The analytical results of each chromatography peak shown in FIGS. 2-10 were shown in the following Table 1-9.

TABLE 1

| | | | Crystals RA-A | | | | | |
|---|---|---|---|---|---|---|---|---|
| CH | PKNO | T | A | H | MK | IDNO | CONC | N |
| 1 | 1 | 4.857 | 6932 | 486 | | | 0.2192 | Stev mono |
| | 2 | 8.817 | 1467 | 107 | | | | |
| | 3 | 9.603 | 2029 | 124 | | | 0.0642 | Rubuso |
| | 4 | 10.244 | 3630 | 214 | | | | |
| | 5 | 11.065 | 12106 | 605 | | | | |
| | 6 | 14.763 | 14947 | 397 | | | 0.4726 | Rebau B |
| | 7 | 16.782 | 58617 | 2320 | | | 1.8535 | Stev |
| | 8 | 18.901 | 35984 | 1440 | | | 1.1379 | Rebau C |
| | 9 | 19.984 | 23401 | 820 | | | 0.7400 | Rebau F |
| | 10 | 23.334 | 2971977 | 97370 | | | 93.9772 | Rebau A |
| | 11 | 28.648 | 4872 | 191 | | | 0.1541 | Rebau E + III + IV |
| | 12 | 34.608 | 5912 | 174 | | | 0.1869 | V + VI + VII |
| | 13 | 35.531 | 28131 | 892 | V | | 0.8895 | Rebau D + VIII |
| | 14 | 37.222 | 5390 | 185 | | | | |
| | 15 | 42.731 | 6943 | 222 | | | 0.2195 | IX |
| | 16 | 51.166 | 2700 | 88 | | | 0.0854 | X |
| | | TOT | 3185038 | 105635 | | | 100.0000 | |

TABLE 2

Crystals RA-B

| CH | PKNO | T | A | H | MK | IDNO | CONC | N |
|---|---|---|---|---|---|---|---|---|
| 1 | 1 | 2.098 | 1307 | 246 | | | | |
| | 2 | 2.309 | 675 | 139 | V | | | |
| | 3 | 2.833 | 7713 | 1426 | | | | |
| | 4 | 4.775 | 3286 | 244 | | | | |
| | 5 | 13.518 | 91704 | 3965 | | | 2.8021 | I |
| | 6 | 14.834 | 14854 | 462 | | | 0.4539 | Rebau B |
| | 7 | 16.077 | 1125 | 54 | | | | |
| | 8 | 16.8 | 747 | 88 | | | | |
| | 9 | 17.034 | 9460 | 352 | V | | 0.2891 | Stev |
| | 10 | 18.601 | 2647 | 110 | | | | |
| | 11 | 19.157 | 7685 | 314 | V | | 0.2348 | Rebau C |
| | 12 | 20.268 | 20421 | 652 | | | 0.6240 | Rebau F |
| | 13 | 23.663 | 3106124 | 102260 | | | 94.9097 | Rebau A |
| | 14 | 27.533 | 2882 | 95 | | | | |
| | 15 | 29.043 | 5444 | 210 | | | 0.1663 | III + Rebau E + IV |
| | 16 | 31.461 | 2828 | 91 | | | 0.0864 | |
| | 17 | 35.959 | 8128 | 282 | | | 0.2484 | Rebau D + V + VI + VII |
| | 18 | 37.696 | 6165 | 183 | | | | |
| | 19 | 43.225 | 4259 | 120 | | | 0.1301 | IX |
| | 20 | 51.644 | 1807 | 53 | | | 0.0552 | X |
| | | TOT | 3299261 | 111346 | | | 100.0000 | |

TABLE 3

Crystals RA-C

| CH | PKNO | T | A | H | MK | IDNO | CONC | N |
|---|---|---|---|---|---|---|---|---|
| 1 | 1 | 2.335 | 15257 | 2745 | | | | |
| | 2 | 3.398 | 2074 | 247 | | | | |
| | 3 | 4.436 | 3292 | 209 | | | | |
| | 4 | 9.657 | 51969 | 2355 | | | 1.6822 | Rubuso |
| | 5 | 14.351 | 4502 | 107 | | | 0.1457 | Rebau B |
| | 6 | 16.175 | 5072 | 189 | | | 0.1642 | Stev |
| | 7 | 18.192 | 2634 | 88 | | | 0.0853 | Rebau C |
| | 8 | 19.366 | 13008 | 474 | | | 0.4211 | Rebau F |
| | 9 | 22.682 | 3002254 | 98794 | | | 97.1825 | Rebau A |
| | 10 | 34.744 | 4564 | 160 | | | 0.1477 | V + VI + Rebau D + VII + VIII |
| | 11 | 36.455 | 3018 | 96 | | | 0.0977 | |
| | 12 | 41.927 | 1880 | 67 | | | 0.0609 | IX |
| | 13 | 50.485 | 393 | 17 | | | 0.0127 | X |
| | | TOT | 3109917 | 105548 | | | 100.0000 | |

TABLE 4

Extract RA-A

| CH | PKNO | T | A | H | MK | IDNO | CONC | N |
|---|---|---|---|---|---|---|---|---|
| 1 | 1 | 2.646 | 12581 | 1924 | | | | |
| | 2 | 3.502 | 1786 | 313 | | | | |
| | 3 | 3.715 | 5140 | 389 | V | | | |
| | 4 | 4.411 | 36010 | 2058 | V | | | |
| | 5 | 4.64 | 18976 | 2043 | V | | | |
| | 6 | 4.904 | 94086 | 5839 | V | | 1.3702 | Stev mono |
| | 7 | 5.683 | 42933 | 1608 | V | | | |
| | 8 | 6.108 | 9264 | 666 | V | | | |
| | 9 | 6.642 | 30742 | 778 | V | | | |
| | 10 | 7.192 | 23108 | 906 | V | | | |
| | 11 | 7.736 | 52867 | 2210 | V | | 0.7699 | Stevbio |
| | 12 | 8.292 | 22402 | 750 | V | | | |
| | 13 | 8.831 | 44958 | 2378 | V | | | |
| | 14 | 9.615 | 104428 | 4765 | V | | 1.5208 | Rubuso |
| | 15 | 10.262 | 92646 | 4531 | V | | | |
| | 16 | 10.917 | 33787 | 1420 | V | | | |

TABLE 4-continued

Extract RA-A

| CH | PKNO | T | A | H | MK | IDNO | CONC | N |
|---|---|---|---|---|---|---|---|---|
|  | 17 | 12.778 | 63372 | 2978 |  |  | 0.9229 | Dulco A |
|  | 18 | 13.466 | 12776 | 658 | V |  | 0.1861 | I |
|  | 19 | 14.821 | 47594 | 1672 |  |  | 0.6931 | Rebau B |
|  | 20 | 16.812 | 2795705 | 107308 |  |  | 40.7133 | Stev |
|  | 21 | 18.95 | 683621 | 23300 | V |  | 9.9554 | Rebau C |
|  | 22 | 20.017 | 130330 | 3792 | V |  | 1.8980 | Rebau F |
|  | 23 | 22.017 | 4444 | 192 |  |  |  |  |
|  | 24 | 23.385 | 2759980 | 90911 |  |  | 40.1931 | Rebau A |
|  | 25 | 26.082 | 15240 | 516 |  |  |  |  |
|  | 26 | 28.592 | 5443 | 144 |  |  | 0.0793 |  |
|  | 27 | 29.425 | 6048 | 234 | V |  | 0.0881 | III + Rebau E |
|  | 28 | 30.066 | 29426 | 961 | V |  | 0.4285 | IV |
|  | 29 | 33.96 | 10732 | 419 |  |  | 0.1563 | V + VI + VII |
|  | 30 | 35.559 | 51215 | 1667 |  |  | 0.7458 | Rebau D + VIII |
|  | 31 | 42.755 | 15644 | 462 |  |  | 0.2278 | IX |
|  | 32 | 51.175 | 3535 | 108 |  |  | 0.0515 | X |
|  | TOT |  | 7260819 | 267900 |  |  | 100.0000 |  |

TABLE 5

Extract RA-B

| CH | PKNO | T | A | H | MK | IDNO | CONC | N |
|---|---|---|---|---|---|---|---|---|
| 1 | 1 | 2.136 | 1244 | 231 |  |  |  |  |
|  | 2 | 2.862 | 8119 | 1484 |  |  |  |  |
|  | 3 | 4.411 | 37288 | 2536 |  |  |  |  |
|  | 4 | 4.634 | 25374 | 2584 | V |  |  |  |
|  | 5 | 4.889 | 113717 | 7669 | V |  | 3.2793 | Stev mono |
|  | 6 | 5.766 | 57184 | 1940 | V |  |  |  |
|  | 7 | 6.666 | 16138 | 503 | V |  |  |  |
|  | 8 | 7.319 | 34921 | 927 | V |  | 0.3964 | Stev bio |
|  | 9 | 7.917 | 13888 | 628 | V |  |  |  |
|  | 10 | 8.533 | 19410 | 741 | V |  |  |  |
|  | 11 | 8.887 | 44852 | 2585 | V |  |  |  |
|  | 12 | 9.35 | 16370 | 1111 | V |  | 0.4751 | Rubuso |
|  | 13 | 9.71 | 81099 | 3752 | V |  |  |  |
|  | 14 | 10.339 | 81250 | 3739 | V |  |  |  |
|  | 15 | 12.183 | 4543 | 172 |  |  |  |  |
|  | 16 | 12.941 | 26992 | 1213 | V |  | 0.5187 | Dulco A |
|  | 17 | 13.658 | 35796 | 1693 | V |  | 0.7239 | I |
|  | 18 | 15.012 | 62182 | 2088 |  |  | 0.8928 | II |
|  | 19 | 17.039 | 1579831 | 61299 |  |  | 26.2115 | Stev |
|  | 20 | 19.212 | 630967 | 21477 | V |  | 9.1836 | Rebau C |
|  | 21 | 20.303 | 129387 | 3817 | V |  | 1.6322 | Rebau F |
|  | 22 | 23.721 | 3953586 | 128495 | S |  | 54.9446 | Rebau A |
|  | 23 | 26.44 | 11802 | 359 | T |  |  |  |
|  | 24 | 29.088 | 9888 | 346 |  |  |  |  |
|  | 25 | 29.817 | 9663 | 299 | V |  |  |  |
|  | 26 | 30.449 | 17347 | 602 | V |  | 0.2574 | Rebau E + III + IV |
|  | 27 | 32.984 | 10425 | 265 |  |  |  |  |
|  | 28 | 34.415 | 15693 | 537 |  |  |  |  |
|  | 29 | 35.159 | 18016 | 574 | V |  | 0.2454 | V + VI + VII |
|  | 30 | 36.025 | 68454 | 2067 | V |  | 0.8839 | Rebau D + VIII |
|  | 31 | 37.749 | 4538 | 157 |  |  |  |  |
|  | 32 | 43.275 | 20100 | 626 |  |  | 0.2677 | IX |
|  | 33 | 51.757 | 7320 | 205 |  |  | 0.0877 | X |
|  | TOT |  | 7167384 | 256711 |  |  | 100.0000 |  |

TABLE 6

Extract RA-C

| CH | PKNO | T | A | H | MK | IDNO | CONC | N |
|---|---|---|---|---|---|---|---|---|
| 1 | 1 | 2.183 | 616 | 134 | | | | |
| | 2 | 2.597 | 10175 | 1537 | | | | |
| | 3 | 3.437 | 1414 | 323 | | | | |
| | 4 | 4.46 | 13740 | 1017 | | | | |
| | 5 | 4.642 | 6308 | 820 | V | | | |
| | 6 | 4.906 | 54449 | 4098 | V | | 0.8853 | Stev mono |
| | 7 | 5.721 | 9947 | 485 | V | | | |
| | 8 | 6.06 | 3281 | 277 | V | | | |
| | 9 | 8.264 | 25348 | 701 | | | | |
| | 10 | 8.844 | 16133 | 1093 | V | | | |
| | 11 | 9.66 | 34116 | 1479 | | | | |
| | 12 | 10.275 | 34888 | 1821 | V | | 0.5673 | Rubuso |
| | 13 | 10.799 | 10225 | 529 | V | | | |
| | 14 | 11.829 | 144125 | 5701 | | | | |
| | 15 | 12.826 | 9263 | 377 | V | | 0.1506 | Dulco A |
| | 16 | 14.874 | 129304 | 2644 | | | 2.1024 | Rebau B |
| | 17 | 16.871 | 437696 | 17109 | V | | 7.1167 | Stev |
| | 18 | 19.001 | 472663 | 16510 | | | 7.6852 | Rebau C |
| | 19 | 20.078 | 99978 | 2988 | V | | 1.6256 | Rebau F |
| | 20 | 23.439 | 4700591 | 156131 | | | 76.4290 | Rebau A |
| | 21 | 26.161 | 6575 | 216 | | | | |
| | 22 | 28.759 | 19933 | 692 | | | | |
| | 23 | 29.523 | 16030 | 496 | V | | 0.2606 | Rebau E |
| | 24 | 30.192 | 4314 | 195 | V | | 0.0701 | III + IV |
| | 25 | 32.915 | 22341 | 361 | | | 0.0000 | |
| | 26 | 34.044 | 20210 | 662 | V | | 0.3286 | V |
| | 27 | 34.784 | 37467 | 1171 | V | | 0.6092 | VI + VII |
| | 28 | 35.637 | 82080 | 2479 | V | | 1.3346 | Rebau D + VIII |
| | 29 | 42.833 | 32965 | 977 | | | 0.5360 | IX |
| | 30 | 51.265 | 18371 | 536 | | | 0.2987 | X |
| | | TOT | 6474546 | 223559 | | | 100.0000 | |

TABLE 7

Extract ST

| CH | PKNO | T | A | H | MK | IDNO | CONC | N |
|---|---|---|---|---|---|---|---|---|
| 1 | 1 | 2.626 | 7139 | 1183 | | | | |
| | 2 | 3.325 | 824 | 127 | | | | |
| | 3 | 3.683 | 3069 | 423 | V | | | |
| | 4 | 3.836 | 9867 | 1104 | V | | | |
| | 5 | 4.1 | 20804 | 2418 | V | | | |
| | 6 | 4.432 | 158950 | 6323 | V | | | |
| | 7 | 4.898 | 244425 | 14003 | V | | 3.2613 | Stev mono |
| | 8 | 5.679 | 171018 | 7277 | V | | | |
| | 9 | 6.067 | 36443 | 2486 | V | | | |
| | 10 | 6.567 | 84143 | 3356 | V | | | |
| | 11 | 6.833 | 59479 | 3255 | V | | | |
| | 12 | 7.702 | 364999 | 10439 | V | | 4.8701 | Stev bio |
| | 13 | 8.831 | 50633 | 2395 | V | | | |
| | 14 | 9.622 | 121367 | 5308 | V | | 1.6194 | Rubuso |
| | 15 | 10.283 | 61202 | 2776 | V | | | |
| | 16 | 10.651 | 82679 | 3615 | V | | | |
| | 17 | 12.789 | 172505 | 7512 | | | 2.3017 | Dulco A |
| | 18 | 13.476 | 39377 | 1734 | V | | 0.5254 | I |
| | 19 | 14.117 | 9126 | 325 | V | | | |
| | 20 | 14.843 | 56080 | 1517 | V | | 0.7483 | Rebau B |
| | 21 | 15.883 | 18828 | 574 | V | | 0.2512 | II |
| | 22 | 16.837 | 4190811 | 160109 | SV | | 55.9165 | Stev |
| | 23 | 18.317 | 837 | 72 | T | | | |
| | 24 | 18.961 | 471940 | 16634 | V | | 6.2969 | Rebau C |
| | 25 | 20.03 | 96159 | 2847 | V | | 1.2830 | Rebau F |
| | 26 | 22.021 | 11777 | 430 | | | | |
| | 27 | 23.407 | 1635704 | 52768 | SV | | 21.8246 | Rebau A |
| | 28 | 26.087 | 18075 | 573 | T | | | |
| | 29 | 30.114 | 37321 | 1256 | | | 0.4980 | Rebau E + III + IV |

TABLE 7-continued

Extract ST

| CH | PKNO | T | A | H | MK | IDNO | CONC | N |
|----|------|---|---|---|----|----|------|---|
|  | 30 | 34.028 | 11847 | 362 |  |  | 0.1581 | V + VI + VII |
|  | 31 | 35.633 | 28790 | 851 | V |  | 0.3841 | Rebau D + VIII |
|  | 32 | 42.867 | 4616 | 125 |  |  | 0.0616 | IX |
|  | TOT |  | 8280834 | 314177 |  |  | 100.0000 |  |

TABLE 8

Crystals ST-ST

| CH | PKNO | T | A | H | MK | IDNO | CONC | N |
|----|------|---|---|---|----|----|------|---|
| 1 | 1 | 2.64 | 20368 | 3347 |  |  |  |  |
|  | 2 | 3.342 | 792 | 150 |  |  |  |  |
|  | 3 | 8.16 | 199715 | 8553 |  |  |  |  |
|  | 4 | 9.579 | 28792 | 1602 |  |  | 0.7198 | Rubuso |
|  | 5 | 13.436 | 6892 | 362 |  |  | 0.1723 | I |
|  | 6 | 16.763 | 3809949 | 146224 | S |  | 95.2514 | Stev |
|  | 7 | 19.017 | 1413 | 63 | T |  | 0.0353 | Rebau C |
|  | 8 | 21.883 | 3078 | 108 |  |  | 0.0770 | Rebau F |
|  | 9 | 23.323 | 138456 | 4564 | V |  | 3.4615 | Rebau A |
|  | 10 | 26.007 | 6455 | 215 |  |  |  |  |
|  | 11 | 30.02 | 11309 | 367 |  |  | 0.2827 | Rebau E + III + IV |
|  | TOT |  | 4227219 | 165555 |  |  | 100.0000 |  |

TABLE 9

Crystals ST-RA

| CH | PKNO | T | A | H | MK | IDNO | CONC | N |
|----|------|---|---|---|----|----|------|---|
| 1 | 1 | 2.567 | 11398 | 2039 |  |  |  |  |
|  | 2 | 3.19 | 846 | 174 |  |  |  |  |
|  | 3 | 11.629 | 43279 | 1893 |  |  |  |  |
|  | 4 | 14.703 | 13970 | 400 |  |  | 0.4290 | Rebau B |
|  | 5 | 15.927 | 1715 | 79 |  |  |  |  |
|  | 6 | 16.885 | 7321 | 220 |  |  | 0.2248 | Stev |
|  | 7 | 18.961 | 4537 | 192 |  |  | 0.1393 | Rebau C |
|  | 8 | 20.055 | 9706 | 413 |  |  | 0.2981 | Rebau F |
|  | 9 | 23.428 | 3204919 | 106088 |  |  | 98.4203 | Rebau A |
|  | 10 | 28.744 | 5579 | 170 |  |  | 0.1713 | Rebau E + III + IV |
|  | 11 | 33.32 | 4707 | 121 |  |  | 0.1445 | V + VI + VII |
|  | 12 | 35.603 | 4198 | 146 |  |  | 0.1289 | Rebau D + VIII |
|  | 13 | 42.8 | 1422 | 45 |  |  | 0.0437 | IX |
|  | TOT |  | 3313597 | 111980 |  |  | 100.0000 |  |

The abbreviations used in the tables above are as follows:
PKNO: Peak Number
T: Time (minutes)
A: Peak area
H: Peak Height
CONC: Concentration (%)
N: Glycoside's Name
TOT: Total
Stev mono: Steviol monoside
Stev bio: Steviol bioside
Rebuso: Rubososide
Rebau: Rebaudioside
Stev: Stevioside
Dulco: Dulcoside The concentration is calculated from the total area of the ultraviolet absorption spectrum at 210 nm, and it is necessary to correct the molecular weight in order to measure the volume contained. I to X in the chromatograph chart indicate the novel Steviol Glycoside I to X.

Example 6 Evaluation of Taste Quality 0.05% aqueous solution of each extract and 0.03% aqueous solution of the crystals were evaluated by 10 people familiar with a sensory test of *Stevia*, and the results of averaged evaluation are shown in Table 10 below: Evaluation 5: Excellent, 4: Good, 3: Ordinary, 2: Bad, 1: Worst

TABLE 10

| Subject matter of the sensory test | 1) | 2) | 3) | 4) | 5) | 6) |
|---|---|---|---|---|---|---|
| RA-A Extract | 4.1 | 3.8 | 4.1 | 4.9 | 3.4 | 3.8 |
| RA-A Crystal | 5.0 | 4.9 | 4.9 | 3.2 | 4.9 | 4.9 |

TABLE 10-continued

| Subject matter of the sensory test | 1) | 2) | 3) | 4) | 5) | 6) |
|---|---|---|---|---|---|---|
| RA-B Extract | 4.2 | 3.8 | 4.1 | 4.9 | 3.5 | 3.7 |
| RA-B Crystal | 5.0 | 5.0 | 4.9 | 3.5 | 4.9 | 4.9 |
| RA-C Extract | 4.2 | 4.0 | 4.5 | 4.8 | 3.5 | 3.8 |
| RA-C Crystal | 5.0 | 5.0 | 5.0 | 3.8 | 5.0 | 5.0 |
| ST Extract | 1.2 | 1.3 | 1.2 | 4.0 | 2.0 | 2.0 |
| ST-RA Crystal | 4.8 | 4.6 | 4.6 | 3.0 | 4.8 | 4.3 |

1) Sweetness Quality
2) Taste remaining in the mouth
3) Astringency
4) Delicate taste
5) Refreshing feeling
6) Sweetness running out The three types of RA Extract containing the Steviol Glycosides II to X (Rebaudioside G to O) are excellent in delicate taste compared to the three types of RA Crystals, but the RA Crystals are excellent in the other evaluations. Except for the delicate taste evaluation, the ST extract is inferior to the ST-RA Crystals. From this result, it is verified that the novel Steviol Glycosides II-X influence the delicate taste.

Example 7 Determination of Variety

According to the HPLC analysis of each extract and/or crystal, the extract obtained from the varieties containing RA as a main component (hereinafter Variety RA) includes more Rebaudioside D, and also include the Steviol Glycoside X (Rebaudioside O) compared with the extract obtained from the varieties containing ST as a main component (hereinafter Variety ST). Further it is found that the Steviol Glycoside X is also included in the RA crystals obtained by the purification of the extract of RA varieties, although trace amount.

On the other hand, there is no Steviol Glycoside X in the extract obtained from the ST varieties. Naturally the Steviol Glycoside X is not found out in the ST-RA crystals obtained from the ST varieties and it is therefore possible to confirm that the extract or the crystal is obtained from the RA variety, if the presence of Steviol Glycoside X is confirmed.

Example 8 Analytical Method of Steviol Glycoside

According to the HPLC condition described in Example 5, it is possible to confirm each Steviol Glycoside I-X. In principle, it is possible to confirm the presence of Steviol Glycoside from R.T. in the HPLC analytical chart, but each Steviol Glycoside I-X can be confirmed by measuring the molecular weight after preparative isolation of each Glycoside.

Example 9 Tabletop Sugar

1) Tabletop sugar was prepared by mixing 1 g of RA-A Crystals and 99 g of powder sugar.
2) Tabletop sugar was prepared by mixing 1 g of RA-B Crystals and 99 g of erythritol.
3) Tabletop sugar was prepared by mixing 1 g of RA-C Crystals and 99 g of high-fructose corn syrup.

Example 10 Candies

Candy was prepared from 0.3 g of RA-C extract, 100 g of palatinit and an appropriate volume of spices.

Example 11 Milk Jelly

Milk jelly was prepared form 15 g of sugar, 0.08 g of RA-B extract, 250 g of milk, 5 g of gelatin and an appropriate volume of milk flavor.

Example 12 Sports Drinks

Sports drink was prepared from 0.075% of RA-B Crystals, 0.11% of calcium lactate, 0.045% of citric acid, 0.03% of trisodium citrate, 0.015% of magnesium chloride, 0.0055% of glutamic acid and 99.72% of water.

Example 13 Carbonate Drinks

Carbonate drink was prepared by adding 0.012% of RA-B Crystals, 8.4% of fructose, 0.6% of citric acid, 0.12% of arginine, 0.1% of inositol, 0.0025% of caffeine, 0.0034% of calcium pantothenate, 0.003% of niacin amide, 0.002% of vitamin B6, 0.00009% of vitamin B2, 0.000002% of vitamin B12, and appropriate volumes of spices and water to adjust 100% of whole ingredients, and then introducing carbon dioxide gas.

INDUSTRIAL APPLICABILITY

By HPLC analysis of the novel Steviol Glycosides provided by the present invention, it is possible to manufacture sweeteners and other foodstuff with a certain sweetness degree and quality, and delicate taste. Also it enables to presume the raw material varieties, and the invention is helpful to judge the correctness of indication of origin, cultivation area of the *Stevia* varieties, or infringement of right.

BRIEF DESCRIPTION OF DRAWINGS

FIG. 1 It shows the HPLC Analysis Chart for the extract RA-C.

FIG. 2 It shows the HPLC Analysis Chart for Crystals RA-A.

FIG. 3 It shows the HPLC Analysis Chart for Crystals RA-B.

FIG. 4 It shows the HPLC Analysis Chart for Crystals RA-C.

FIG. 5 It shows the HPLC Analysis Chart for the extract RA-A.

FIG. 6 It shows the HPLC Analysis Chart for the extract RA-B.

FIG. 7 It shows the HPLC Analysis Chart for the extract RA-C.

FIG. 8 It shows the HPLC Analysis Chart for the extract ST.

FIG. 9 It shows the HPLC Analysis Chart for Crystals ST-ST.

FIG. 10 It shows the HPLC Analysis Chart for Crystals ST-RA.

The invention claimed is:

1. A method of manufacturing of a sweetener comprising Steviol glycoside VIII (Rebaudioside M) of the formula:

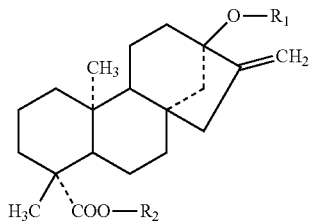

wherein $R_1$ and $R_2$ represent sugar chains defined in the following table;

| No. | $R_1$ | $R_2$ |
|---|---|---|
| VIII | β-glc-β-glc(2→1)<br>　＼β-glc(3→1) | β-glc-β-glc(2→1)<br>　＼β-glc(3→1) | the method comprising:
purifying the Steviol glycoside VIII such that the Steviol glycoside VIII is separated from Rebaudioside A and formulating the sweetener with the Steviol glycoside VIII; wherein the sweetener comprises a larger amount of the Steviol glycoside VIII than any other Steviol glycoside.

2. The method of claim 1, wherein the Steviol glycoside VIII is purified from *Stevia rebaudiana* Bertoni.

3. The method of claim 1, further comprising crystalizing an extract obtained from the purifying step.

4. The method of claim 1, wherein the purifying comprises use of a column.

5. The method of claim 4, further comprising crystalizing an extract obtained from the purifying step.

6. The method of claim 5, wherein the crystals comprise a larger amount of the Steviol glycoside VIII than Rebaudioside A.

7. The method of claim 5, wherein the crystals comprise a larger amount of the Steviol glycoside VIII than any other Steviol glycoside.

8. The method of claim 1, wherein the purifying comprises adsorbing the Steviol glycoside VIII to an adsorbant resin and eluting the Steviol glycoside VIII from the adsorbant resin to produce an extract.

9. The method of claim 8, further comprising crystalizing the extract obtained from the purifying step.

10. The method of claim 8, wherein the extract comprises a larger amount of the Steviol glycoside VIII than any other Steviol glycoside.

11. The method of claim 1, wherein an extract obtained from the purifying step comprises a larger amount of the Steviol glycoside VIII than Rebaudioside A.

12. A method of preparing a food product, the method comprising
manufacturing the sweetener according to the method of claim 1, and
mixing the sweetener and a food to form the food product.

13. A method of preparing a food product, the method comprising
manufacturing the sweetener according to the method of claim 4, and
mixing the sweetener and a food to form the food product.

14. A method of preparing a food product, the method comprising
manufacturing the sweetener according to the method of claim 5, and
mixing the sweetener and a food to form the food product.

15. A method of extracting Steviol glycoside VIII (Rebaudioside M) from a solution of Steviol glycoside VIII and water or a solvent containing water, comprising extracting the solution with water or a solvent containing water to form an extract comprising the Steviol glycoside VIII, wherein the extract comprises a higher concentration of Steviol glycoside VIII than the solution, and the extract comprises a larger amount of the Steviol glycoside VIII than any other Steviol glycoside wherein the Steviol glycoside VIII has the formula:

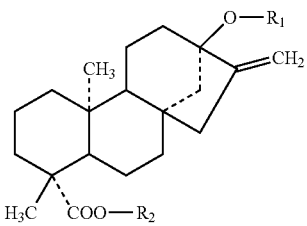

wherein $R_1$ and $R_2$ represent sugar chains defined in the following table

| No. | $R_1$ | $R_2$ |
|---|---|---|
| VIII | β-glc-β-glc(2→1)<br>　＼β-glc(3→1) | β-glc-β-glc(2→1)<br>　＼β-glc(3→1) |

16. The method of claim 15, wherein the extract comprises a lower concentration of Rebaudioside A compared to the Rebaudioside A concentration in the solution.

17. The method of claim 15, wherein the extracting comprises use of a column.

18. The method of claim 16, wherein the extracting comprises use of a column.

19. The method of claim 15, wherein the extracting comprises use of a resin adsorbing Steviol glycosides.

20. The method of claim 1, wherein the purifying comprises purifying the Steviol glycoside VIII from a *Stevia rebaudiana* Bertoni variety which contains more Rebaudioside A content than Stevioside.

21. The method of claim 15, wherein the solution is obtained from a *Stevia rebaudiana* Bertoni variety which contains more Rebaudioside A content than Stevioside.

* * * * *